(12) United States Patent
Feinberg

(10) Patent No.: US 11,607,137 B2
(45) Date of Patent: Mar. 21, 2023

(54) SYSTEM AND METHOD FOR NONINVASIVE MEASUREMENT OF CENTRAL VENOUS PRESSURE

(71) Applicant: Jack Leonard Feinberg, Manhattan Beach, CA (US)

(72) Inventor: Jack Leonard Feinberg, Manhattan Beach, CA (US)

( * ) Notice: Subject to any disclaimer, the term of this patent is extended or adjusted under 35 U.S.C. 154(b) by 628 days.

(21) Appl. No.: 16/504,176

(22) Filed: Jul. 5, 2019

(65) Prior Publication Data

US 2020/0008684 A1 Jan. 9, 2020

Related U.S. Application Data

(60) Provisional application No. 62/694,994, filed on Jul. 7, 2018.

(51) Int. Cl.

| | |
|---|---|
| *A61B 5/0205* | (2006.01) |
| *H04N 5/272* | (2006.01) |
| *G06T 7/00* | (2017.01) |
| *A61B 5/00* | (2006.01) |
| *G06T 7/20* | (2017.01) |
| *A61B 5/318* | (2021.01) |

(Continued)

(52) U.S. Cl.
CPC ............ *A61B 5/0205* (2013.01); *A61B 5/318* (2021.01); *A61B 5/7278* (2013.01); *A61B 5/7425* (2013.01); *A61B 5/7475* (2013.01); *G06T 7/0012* (2013.01); *G06T 7/20* (2013.01); *H04N 5/272* (2013.01); *A61B 5/02108* (2013.01); *A61B 5/02444* (2013.01); *G06T 2207/10016* (2013.01); *G06T 2207/30101* (2013.01); *G06T 2207/30196* (2013.01)

(58) Field of Classification Search
CPC .............. A61B 5/0205; A61B 5/02108; A61B 5/02152; A61B 5/02444; A61B 5/318; A61B 5/7278; A61B 5/7425; A61B 5/7475; G06T 2207/10016; G06T 2207/30101; G06T 2207/30196; G06T 5/10; G06T 5/20; G06T 7/0012; G06T 7/20; H04N 5/272
See application file for complete search history.

(56) References Cited

U.S. PATENT DOCUMENTS

| | | | |
|---|---|---|---|
| 5,040,540 A | 8/1991 | Sackner | |
| 8,879,867 B2 * | 11/2014 | Tanaka | G01J 3/0264 345/589 |

(Continued)

OTHER PUBLICATIONS

Borst, et al., Exact determination of the central venous pressure by a simple clinical method, The Lancet, Aug. 16, 1952, pp. 304-309.
Caramelo, et al., Comparative study on central venous pressure evaluation in jugular or subclavian and femoral accesses, Critical Care, 2006, 10(Suppl 1): P353.
Chiaco, et al., The jugular venous pressure revisited, Cleve Clin J Med., 2013, 80(10):638-44.

(Continued)

*Primary Examiner* — Jonathan T Kuo
(74) *Attorney, Agent, or Firm* — Knobbe, Martens, Olson & Bear, LLP

(57) ABSTRACT

A non-invasive method of calculating the central venous pressure (CVP) of a patient may include analysis of video of the neck region of the patient. Filters, which may include spatial filters and/or temporal filters, may be applied to the video to enhance the visibility of small movements, which may be due to circulatory pulsations of the patient. The video may be modified to highlight such movements, and motion indicative of venous pulsation may be distinctly identified and highlighted.

20 Claims, 10 Drawing Sheets

(51) Int. Cl.
*A61B 5/024* (2006.01)
*A61B 5/021* (2006.01)

(56) References Cited

U.S. PATENT DOCUMENTS

| | | | |
|---|---|---|---|
| 9,019,305 B2* | 4/2015 | Baumgart | A61B 6/463 345/629 |
| 9,811,901 B2 | 11/2017 | Wu et al. | |
| 10,080,528 B2* | 9/2018 | DeBusschere | A61B 5/1072 |
| 10,217,218 B2 | 2/2019 | Wu et al. | |
| 10,791,982 B2* | 10/2020 | Littell | A61B 5/14553 |
| 2010/0056936 A1* | 3/2010 | Fujii | G01F 1/00 600/504 |
| 2010/0259550 A1* | 10/2010 | Baumgart | A61B 6/463 345/157 |
| 2014/0205175 A1* | 7/2014 | Tanaka | G06T 5/007 382/274 |
| 2017/0049377 A1* | 2/2017 | Littell | A61B 5/032 |
| 2018/0177464 A1* | 6/2018 | DeBusschere | A61B 5/742 |

OTHER PUBLICATIONS

Drazner, et al., Value of clinician assessment of hemodynamics in advanced heart failure: the Escape trial, Circulation Heart Failure, 2008, 1:170-177.

Ewy, Evaluation of the Neck Veins, Hospital Practice, 1987, 22(3A):72-5, 79-80.

Ewy, et al., Bedside estimation of the venous pressure, The Heart Bulletin, May-Jun. 1968, vol. 17:41-44.

Leeuw, Measuring the central venous pressure with the jugular pulse wave, Ned Tijdschr Geneeskd (The Dutch Journal of Medicine) 1999; 143: No. 33, pp. 1692-1696.

Lewis, Early signs of cardiac failure of the congestive type, British Medical Journal, 1930, 1(3618):849-852.

Pahlevan, et al., Noninvasive iPhone Measurement of Left Ventricular Ejection Fraction Using Intrinsic Frequency Methodology, Critical Care Medicine, 2017, 45(7):1115-1120.

Van't Laar, Why is the measurement of jugular venous pressure discredited?, Netherlands Journal of Medicine, 2003, vol. 61, No. 7, pp. 268-272.

Warner et al., Using the Cardiovascular Physical Exam to Full Advantage, Contemporary Internal Medicine, 1992, pp. 51-76.

* cited by examiner

SYSTEM AND METHOD FOR NONINVASIVE MEASUREMENT OF CENTRAL VENOUS PRESSURE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

Embodiments of this disclosure relate to noninvasive measurements of central venous pressure (CVP) in humans.

Description of Related Technology

The central venous pressure (CVP) is the pressure at the junction of the superior vena cava and the right atrium of the heart. Measuring the CVP is an important part of the physical examination. The measurement of CVP can have a diagnostic as well as a therapeutic value.

Measurement of CVP may assist, for example, in the diagnosis of congestive heart failure if the CVP is elevated, particularly in patients with shortness of breath. An elevated CVP may be indicative of congestive heart failure, whereas a normal CVP does not support this diagnosis. In the case of acute shortness of breath, measurement of the CVP is of diagnostic utility, as an increased value suggests heart failure or pulmonary embolism, while a normal value suggests causes such as pulmonary airway obstruction.

Monitoring the CVP is also a simple way of following the effect of treatment in a patient with heart failure. A decrease in the CVP following treatment indicates an improvement in the patient's heart failure.

A normal CVP waveform, reflective of CVP as a function of time, contains three peaks (a, c, and v) corresponding to various aspects of the cardiac cycle. The first peak is the a-wave, which is the result of atrial contraction, peaking near the time of the first heart sound. Shortly after the a-wave there is a second peak, the c-wave, which is a pressure increase due to the tricuspid valve bulging into the atrium as a result of isovolumic ventricular contraction. One goal in the measurement of CVP is to estimate the right ventricular filling or end diastolic pressure, while the tricuspid valve is open. Therefore, the location of the top of the venous pulse just preceding the c-wave is used when estimating jugular venous pressure.

If the tricuspid valve is incompetent, leaking during ventricular contraction, there may be a large v-wave that represents the force of right ventricular contraction, rather than the filling pressure from the right atrium. There are other causes that increase the height of the a-wave or v-wave that are due to anatomic abnormalities in the tricuspid valve, or due to an atrial septal defect.

The CVP may be estimated by controlling the tilt angle of a supine patient while observing the jugular pulse. However, it takes considerable training and experience for an examiner to accurately locate and identify jugular venous pulsations. Additionally, carotid arterial pulsations may be confused with jugular venous pulsations.

The CVP can be measured via a pressure transducer attached to a central venous catheter inserted into the right internal jugular vein and guided into the right atrium of the heart. However, this method is invasive and not without possible medical complications. Risks of catherization include bleeding, damage or puncture of the blood vessels, as well as pain at the catherization site.

SUMMARY

In one broad aspect, a system is described for processing video data by a processing device to provide overlay image data enhancing the display of venous pulsations of a patient, the system including a processor and a memory, the system configured to receive a real-time video stream including image data of a patient, apply a filter to the video stream to facilitate detection of changes between frames of the image data indicative of circulatory pulsations of the patient, and output a modified video stream substantially contemporaneously with the reception of the video stream, the modified video stream including overlay image data indicative of venous pulsations of the patient.

Applying a filter to the video stream may include applying a temporal bandpass filter to the video stream. Applying a filter to the video stream may include applying a spatial filter to the video stream prior to applying a temporal filter.

The system may also be configured to receive a cardiac signal, the cardiac signal indicative of cardiac activity of the patient during capture of the video stream, where the overlay image data is generated at least in part on the received cardiac signal. The system may also be configured to identify at least one venous pulsation time-window and at least one arterial pulsation time-window based on the cardiac signal, where the overlay image data is generated based at least in part on the identified venous pulsation time-window and the identified arterial pulsation time-window. The cardiac signal may include electrocardiogram data.

The overlay image data may highlight motion indicative of venous pulsations of the patient in a first color and other motion in at least one other color distinct from the first color. The system may be configured to record an indication of movement within a subregion of the video stream and display a plot of the movement within the subregion of the video stream over time, and the subregion of the video stream may be identified based at least in part on user input.

In another broad aspect, a system is described, the system configured to estimate the central venous pressure of a patient, the system including a processor and a memory, the system configured to receive a video stream including image data of a patient, receive an indication of the tilt angle of a neck region of the patient, analyze the video stream to identify motion indicative of venous pulsation of the patient, and in response to an indication that the patient is at a representative tilt angle, estimating a central venous pressure of the patient based at least in part on the indication that the patient is at a representative tilt angle.

The indication that the patient is at a representative tilt angle may be received from user input. The system may be further configured to generate overlay data distinguishing the identified motion indicative of venous pulsation from other identified motion in the video stream. The system may be further configured to determine that the patient is at a representative tilt angle without user input subsequent to reception of the video stream. The representative tilt angle may correspond to a position in which the venous pulsations extend to roughly the midpoint of the neck of the patient.

In another broad aspect, a method is described of processing video data by a processing device to provide overlaid image data enhancing the display of venous pulsations of a patient, the method including receiving a video stream including image data of a patient, receiving a cardiac signal indicative of the cardiac activity of the patient, analyzing the video stream to detect motion indicative of venous pulsations of the patient, and modifying the video stream to highlight motion indicative of venous and/or arterial pulsations of the patient.

Analyzing the video stream may include analyzing the video stream based at least in part on the cardiac signal. The cardiac signal may include an electrocardiogram signal. Receiving the cardiac signal may include wirelessly receiving the cardiac signal.

Analyzing the video stream may include applying a temporal filter to the video stream to identify motion indicative of circulatory pulsations, and analyzing the cardiac signal to characterize the detected motion as indicative of arterial or venous pulsations. Analyzing the video stream may include applying a spatial filter to the video stream prior to application of the temporal filter to the video stream. Modifying the video stream to highlight the motion indicative of venous and/or arterial pulsations of the patient may include highlighting the motion indicative of venous pulsations of the patient in a first color and highlighting motion indicative of arterial pulsations in a second color distinct from the first color.

In another broad aspect, a method is described of estimating central venous pressure of a patient, the method including receiving a video stream including image data of a patient, receiving an indication of the tilt angle of a neck region of the patient, modifying the video stream to highlight motion including motion indicative of venous pulsation, and in response to an indication that the patient is at a representative tilt angle, estimating a central venous pressure of the patient based at least in part on the indication of the tilt angle of the patient.

The indication that the patient is at a representative tilt angle may be received from user input. A computing device may determine that the patient is at a representative tilt angle without user input subsequent to reception of the video stream. The representative tilt angle may correspond to a position in which the venous pulsations extend to roughly the midpoint of the neck of the patient.

In another broad aspect, a method is described of processing video data by a processing device to provide overlaid image data enhancing the display of circulatory pulsations of a patient, the method including receiving a real-time video stream including image data of a patient, applying a filter to the video stream to detect changes between frames of the image data indicative of circulatory pulsations of the patient, and outputting a modified video stream substantially contemporaneously with the reception of the video stream, the modified video stream including overlaid image data indicative of the circulatory pulsations of the patient.

The method may additionally include receiving a cardiac signal indicative of cardiac activity of the patient during capture of the video stream, where the overlaid image data is generated at least in part on the received cardiac signal. The method may additionally include identifying at least one venous pulsation window and at least one arterial pulsation window based on the cardiac signal. The overlaid image data may be generated based at least in part on the identified venous pulsation window and the identified arterial pulsation window. The cardiac signal may include electrocardiogram data. The overlaid image data may be indicative of venous pulsation within a jugular vein of the patient.

Applying a filter to the video stream may include applying a temporal bandpass filter to the video stream. The method may additionally include applying a spatial filter to the video stream prior to applying the temporal bandpass filter. The overlaid image data may be indicative of the presence or absence of circulatory pulsation within a subregion of the video stream. The overlaid image data may be indicative of the presence or absence of venous pulsation within a subregion of the video stream. The subregion of the video stream may be identified based at least in part on user input.

BRIEF DESCRIPTION OF THE DRAWINGS

Embodiments of this disclosure will now be described, by way of non-limiting example, with reference to the accompanying drawings.

DETAILED DESCRIPTION OF CERTAIN EMBODIMENTS

Figure 1:
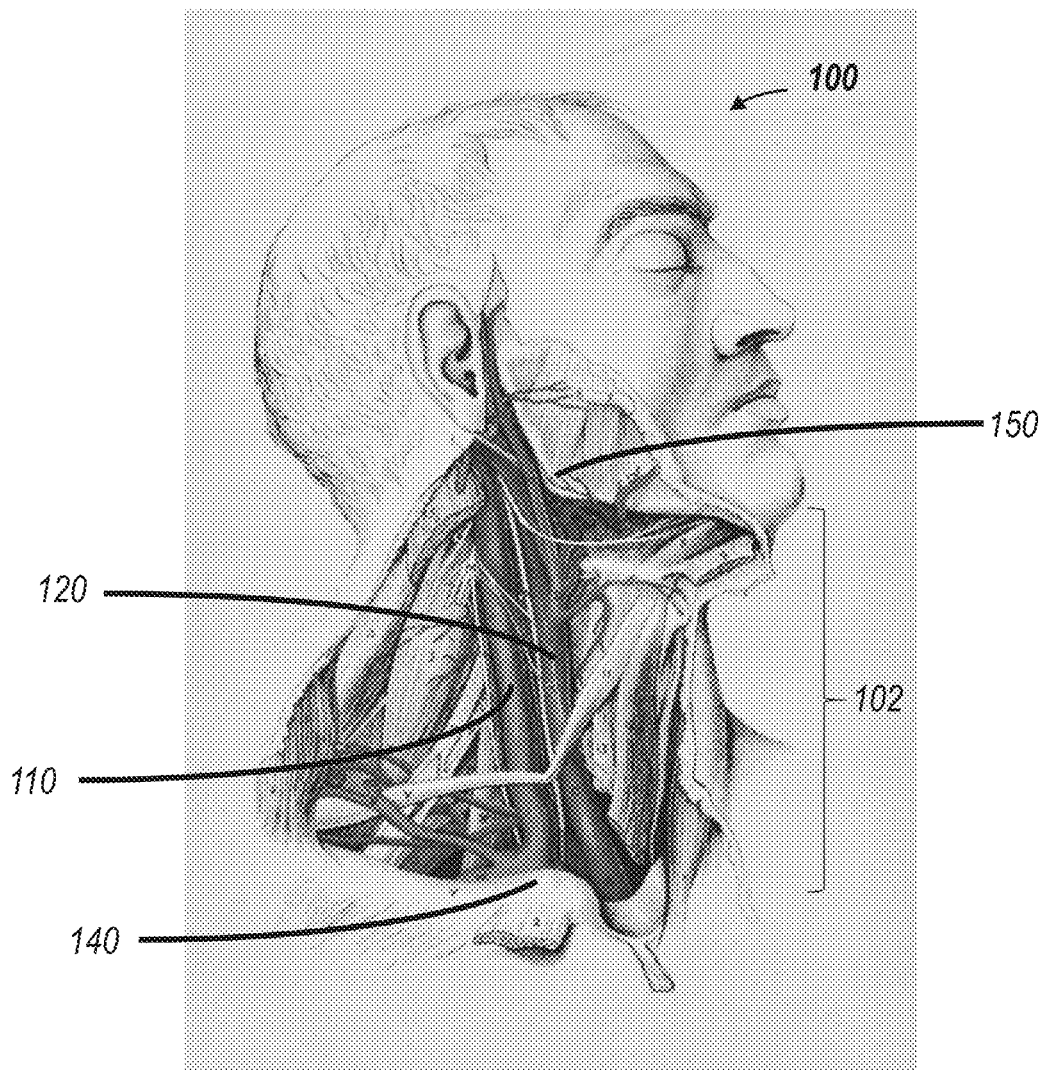
FIG. 1 is an illustration depicting a portion of the internal anatomy of the neck of a patient.

The following description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

Embodiments discussed herein relate to non-invasive systems and methods for evaluating the central venous pressure of a human patient. A video camera may be used to capture video or image data of small movements of one of the jugular veins in the neck. The video image may be processed in real time using a computer program that enhances small motions such as jugular pulsations of the neck, thereby increasing the visibility of such pulsations on a video display. In some embodiments, systems or programs may also display the electrocardiogram of the patient. The pulsations highlighted in the video display may be color coded according to where they occur in the cycle of the patient's electrocardiogram, or the video may be otherwise altered to display such indications.

In some embodiments, an operator can select a specific region of the image on the display using a touch-sensitive screen or a computer mouse. The system may then plot the motion of the selected region in real time. One or both of the motion of the selected region and the electrocardiogram may be converted to audible sounds. By comparing the motion of the selected region with the electrocardiogram, either visually and/or audibly, an observer can distinguish between motion caused by pulsations of a jugular vein versus motion caused by a carotid artery.

When the heart beats, it causes pulsations in blood vessels. Pulsations are evident in all arteries, irrespective of the orientation of the person, but only in some veins. Because of gravity, the walls of a person's veins collapse when the vein's vertical height above the right atrium exceeds the central venous pressure, which may be expressed in cm of water. For example, if a healthy person with a central venous pressure of 5 cm of water is standing upright, veins located more than 5 cm above the right atrium will be in a collapsed state. Collapsed veins do not pulsate.

FIG. 1 is an illustration depicting a portion of the internal anatomy of the neck 102 of a patient 100. On each side of the neck there is an internal and an external jugular vein, as well as a carotid artery. As shown in FIG. 1, the portion of a jugular vein 110 in neck 102 of patient 100 lies close to a carotid artery 120. Pulsations of jugular vein 110 and carotid artery 120 may be visible in an observable region extending between the clavicle 140 and the mandible 150. The observable region of a jugular vein 110 or a carotid artery 120 may extend between a location at or distal of a point at which a jugular vein 110 or a carotid artery 120 extends past the top of clavicle 140 and a location at or proximal of a point at which that jugular vein or carotid artery extends beneath the bottom of mandible 150. Depending on the anatomy of a particular patient, pulsations in the portions of a jugular vein or carotid artery immediately adjacent the bottom of mandible 150 or the top of clavicle 140 may not be observable. Because the height of the venous pulsations is primarily dependent upon the vertical distance from the right atrium of the heart, there is no difference in the height of the venous pulsations on the neck for the internal jugular veins as compared to the external jugular veins. If patient 100 is a healthy person, standing upright, no jugular pulsations will be observed, as the vertical distance from the right atrium to middle of the neck is approximately 20 cm, significantly higher than the venous pressure of 5 cm of water. Jugular veins in the neck will remain collapsed. In contrast, arterial pulsations may be visible even when the healthy patient is upright.

If patient 100 is instead lying on a table or bed, venous pulsations of jugular vein 100, also referred to herein as jugular pulsations, may be observed in addition to arterial pulsations of carotid artery 120. However, these venous pulsations often have multiple peaks per heartbeat. Arterial pulsations will only have one peak per heartbeat. The timing of the pulsations relative to the electrical activity in the heart will also differ for venous and arterial pulsations. The differences in pulsations may be difficult to discern visually. In some embodiments, however, additional information may be utilized to aid in the characterization of pulsation. For example, in some embodiments, variations in pulsation as a function of a tilt angle of the patient's upper body with respect to the horizontal may be used to characterize pulsation as venous or arterial.

Figure 2A:
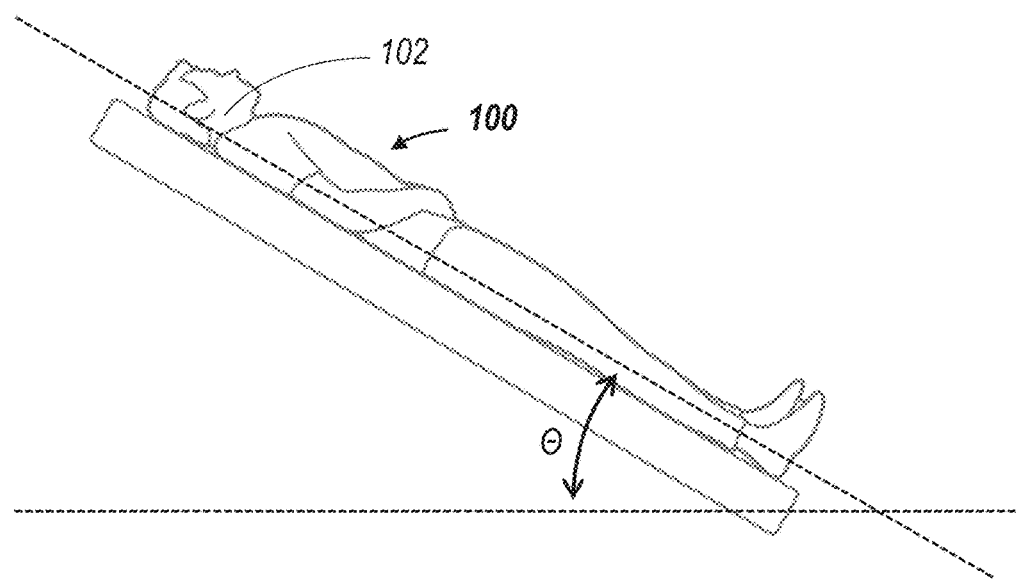
FIG. 2A schematically illustrates a patient supported by a tiltable table which allows the entire body of a patient to be tilted at an angle to the horizontal.
Figure 2B:
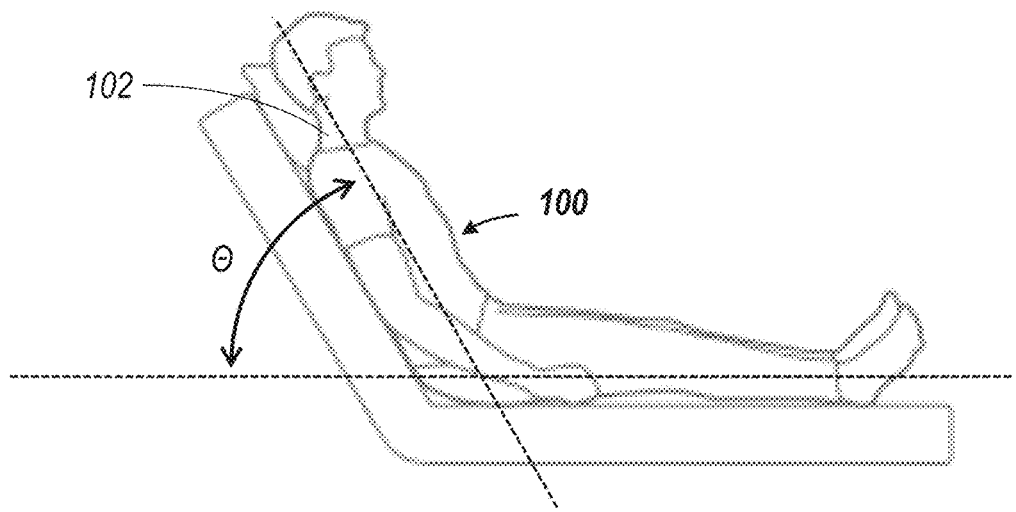
FIG. 2B schematically illustrates a patient supported by a bed or chair that allows the upper body of the patient to be tilted at an angle to the horizontal.

A patient may lie on a table or bed which allows the patent to be tilted at an angle $\theta$ with respect to the horizontal. FIG. 2A schematically illustrates a patient supported by a tiltable table which allows the entire body of a patient to be tilted at an angle to the horizontal. FIG. 2B schematically illustrates a patient supported by a bed or chair that allows the upper body of the patient to be tilted at an angle to the horizontal. The jugular pulsations seen in the neck depend on the central venous pressure of the patient as well as the tilt angle $\theta$ of the patient. The amplitude of the arterial pulsations seen in the neck will remain constant even as the tilt angle $\theta$ of the patient changes. For a given location on the neck of the patient, the character of the pulsations at that location may change as the tilt angle $\theta$ increases, moving from a combination of arterial and venous pulsations at a horizontal position, where $\theta=0$, to only purely arterial pulsations at a vertical position, once the tilt angle $\theta$ is increased to ninety degrees.

The transition in pulsation character at a given location on the neck of patient 100 from arterial and venous pulsations to purely arterial pulsations will occur at a discrete transition tilt angle $\theta_T$, the value of which is dependent upon the CVP of patient 100 and the position of the location being observed on the neck of patient 100. In one embodiment, a particular location may be observed, and the tilt angle $\theta$ varied until a transition tilt angle $\theta_T$ is identified by the cessation of venous pulsations at the observed location. Using that identified tilt angle, a computer algorithm or lookup table may be used to determine the CVP of the patient. In some embodiments, the particular location may be located at the approximate center of neck region 102 of patient 100, between mandible 150 and clavicle 140 of the patient. The particular location may be marked or otherwise identified to allow tracking of the location as the tilt angle $\theta$ changes.

In other embodiments, the tilt angle $\theta$ of the patient may be moved through a plurality of discrete tilt angles, and the location of the venous pulsations identified at each location. For example, the distalmost position of the venous pulsations in the neck may be recorded for each of the plurality of tilt angles. An algorithm or software module may then determine the CVP of the patient from the observed locations of the venous pulsations at each of the plurality of tilt angles.

Figure 3:
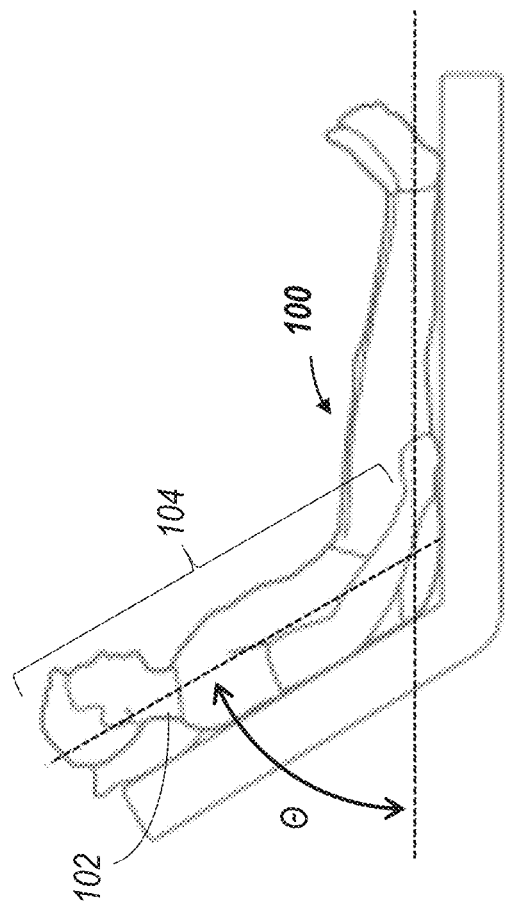
FIG. 3 schematically illustrates a system for determining the CVP of a patient.
Figure 3:
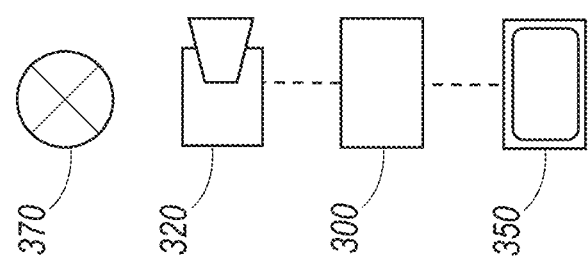

FIG. 3 schematically illustrates a system for determining the CVP of a patient. Patient 100 may be positioned supine, with at least the upper body 104 of patient 100 oriented at an adjustable tilt angle to the horizontal. Supplemental illumination to neck region 102 of patient 100 may be provided by one or more supplementary illumination sources 370. A video camera 320 or other image acquisition device captures image data of at least neck region 102 of patient 100. The image data may be, for example, video recorded at a suitable frame rate.

Video camera 320 is in communication with or forms a component of an image acquisition and processing device 300. Processing device 300 can apply one or more filters to the image data and highlight moving objects in the scene captured by the image data. The filters may include spatial filters and/or temporal filters. The motion-enhanced image may be displayed on a display 350, such as by overlaying motion information on top of the original image data.

In some embodiments, the system may include or be implemented on a smartphone, tablet, or laptop computer. The system could use an integrated camera built into a computing device, and/or an external camera connected to a computing device. The camera, or a computing device including a camera, may be affixed to a stable stand, or tripod, to minimize spurious motion in the scene. The operator may touch the image displayed on the smartphone with a finger or suitable stylus to display, in graphical form, the motion of that portion of the image, and to confirm that the motion in the neck is due to jugular pulsations and not arterial pulsations.

Figure 4:
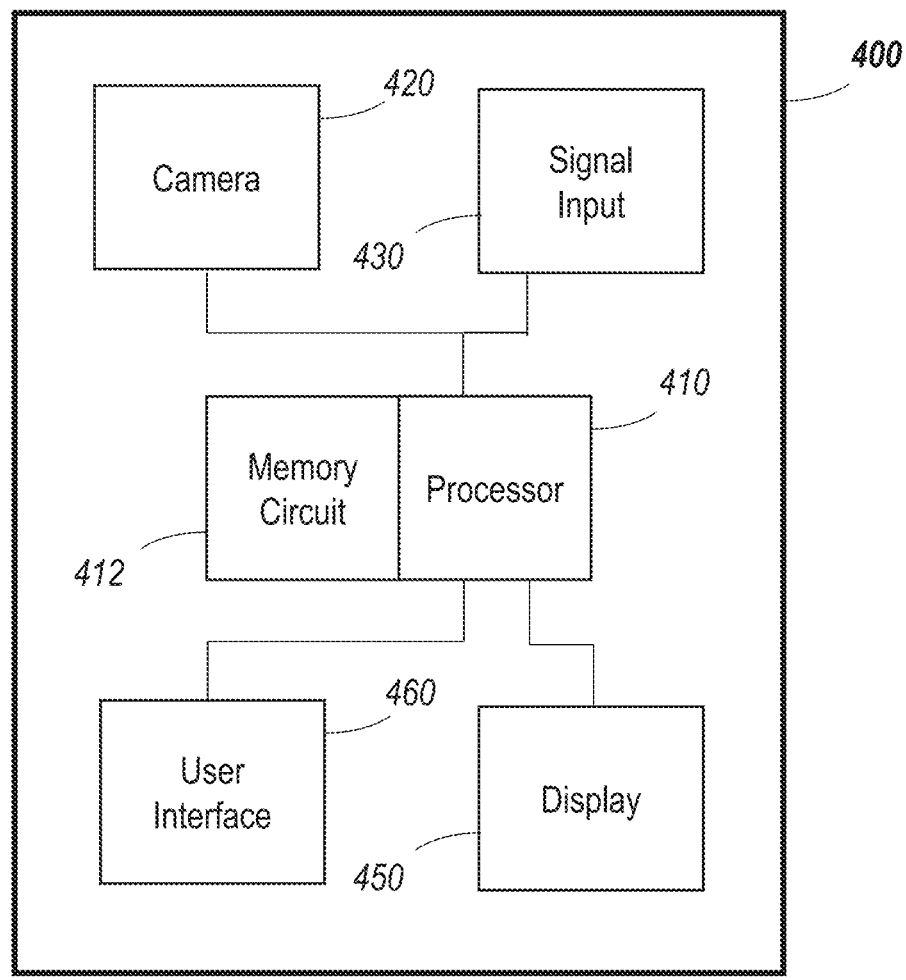
FIG. 4 schematically illustrates an embodiment of a computing device configured to modify video of a patient to highlight circulatory pulsations.

FIG. 4 schematically illustrates an embodiment of a computing device configured to modify video of a patient to highlight circulatory pulsations. The computing device 400 may in some embodiments be a device with an integrated camera 420 and integrated display 450, such as a smartphone or tablet. In other embodiments, computing device 400 may be a personal computer, such as a desktop computer or a laptop computer, and one or both of a camera and display may be external to computing device 400.

Computing device 400 includes a processor 410 in communication with a memory circuit 412. Camera 420 is in communication with processor 410 and memory circuit 412, and computing device 400 may be configured to write video data generated by camera 420 to memory circuit 412. In an embodiment in which the video data will be spatially filtered, a camera 420 having low spatial resolution may be used.

Computing device 400 may in some embodiments be configured to receive a cardiac signal indicative of the cardiac activity of the patient. In some embodiments, the cardiac signal may be an ECG (electrocardiogram) signal, or a signal indicative of an ECG signal. In some embodiments, the cardiac signal may be a video signal, such as a video signal of an external device displaying information indicative of the cardiac activity of a patient. In some embodiments, the cardiac signal may be an audio signal which provides or can be analyzed to provide information regarding the cardiac activity of the patient.

Computing device 400 may receive a cardiac signal in a variety of ways, depending on the nature of the cardiac signal and the manner in which it is generated or provided to computing device 400. In some embodiments, the cardiac signal may be an ECG signal or similar signal provided wirelessly to computing device 400. In such embodiments, a wireless transceiver of computing device 400 may serve as the signal input 430, and may receive the cardiac signal via WiFi, Bluetooth, or any other suitable wireless protocol. In some embodiments, the cardiac signal may be provided via a wired connection, and signal input 430 may be a physical port of computing device 400. In an embodiment in which the cardiac signal is an audio or video signal, camera 420 or audio circuit of computing device 400 may serve as signal input 430.

Computing device 400 may also be configured to receive data indicative of the tilt angle of patient 100. In some embodiments, the tilt angle data may be manually entered by a user after measurement of the tilt angle, such as through the use of a protractor. In some embodiments, the tilt angle may be provided by an external device, such as a tilt table or motorized bed. The external device may include an attached or integrated sensor for detecting the tilt angle, or may include control circuitry able to determine a tilt angle based on prior movement of the tilt angle or motorized bed.

In some embodiments, the tilt angle data may be determined by computing device 400. In some embodiments, this determination may be made through analysis of the video data or other image data. In some embodiments, camera 420 and/or computing device 400 may be fixedly secured relative to a tiltable portion of a tilt table or other patient-supporting device such that the computing device tilts along with the tilt table, to minimize relative motion of the patient with respect to camera 420. In such embodiments, an orientation sensor or other sensor integral to computing device 400 may be used to determine the tilt angle data.

Computing device 400 may include integrated display 450, as discussed above, or may be in communication with an external display through a wireless or wired connection. Computing device 400 may be configured to display a modified video stream, substantially in real-time, which has been modified to highlight or otherwise emphasize cardiovascular pulsations such as venous pulsations of the patient. A display integrated in or in communication with computing device 400 may also display information such as an estimated central venous pressure, a current tilt angle, or a representation of the cardiac activity of the patient.

A user interface 460 may be used to receive user input, such as a selection of a particular region of the video stream. In an embodiment in which computing device 400 includes integrated display 450, user interface 460 may include a touchscreen overlying display 450. In other embodiments, user interface 460 may include a keyboard and/or mouse interface.

Figure 5:
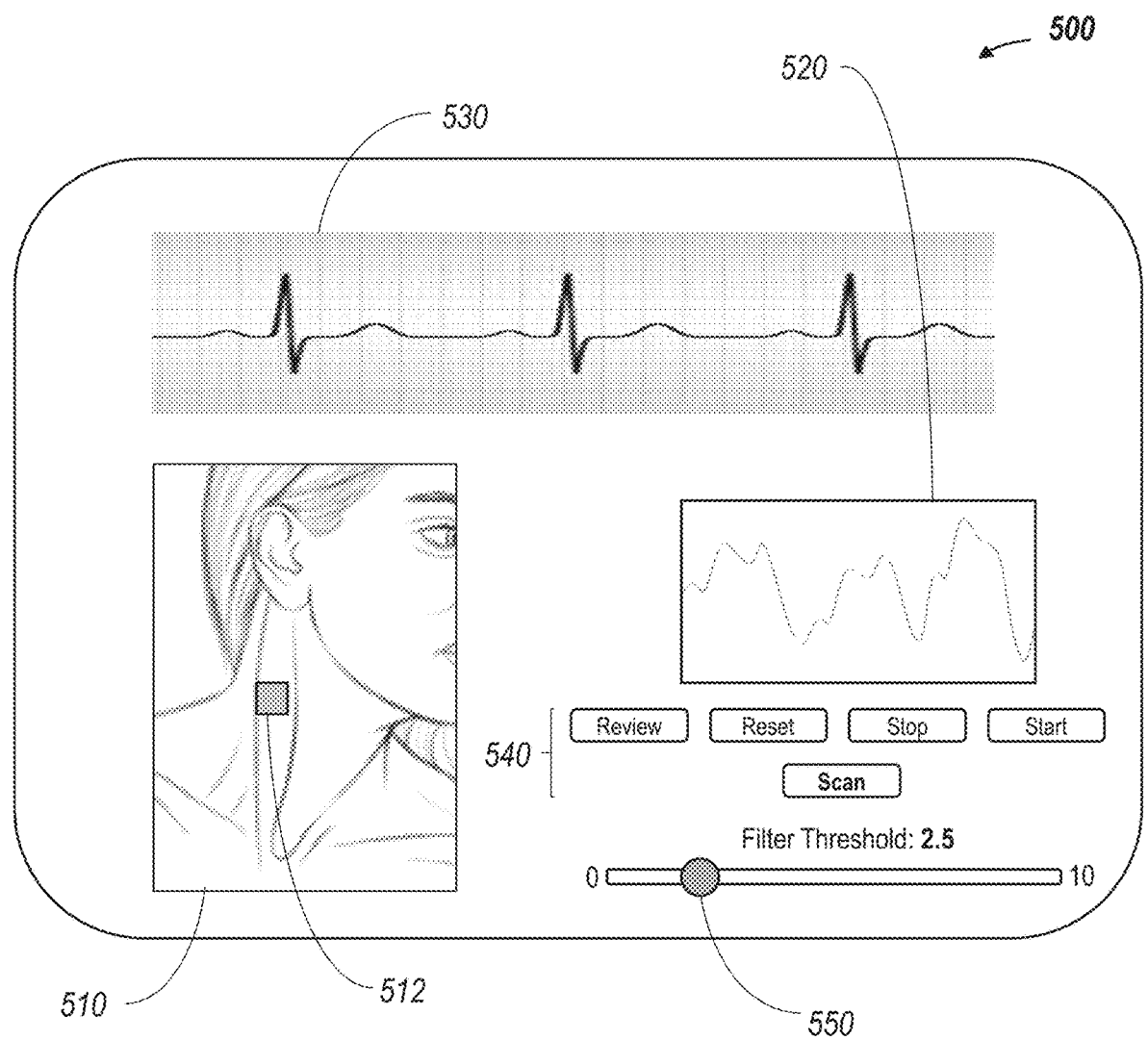
FIG. 5 illustrates an exemplary interface format for a system for determining the CVP of a patient.

FIG. 5 illustrates an exemplary interface format for a system for determining the CVP of a patient. An interface 500 may be displayed on a screen of a smartphone or tablet, or on an external display of a computing device. Interface 500 includes a motion-enhanced video display region 510 which may display video or images including the neck region of the patient, overlaid with motion-enhanced image data generated by the application of one or more filters to the video data. The filters may be computationally efficient filters which allow the modified video data to be displayed in the video display region in substantially real-time.

In some embodiments, an operator may select a particular pixel or region 512 within video display region 510. This selection may be done, for example, by touching or clicking on a specific subregion of video display region 510. In other embodiments, a particular location within video display region 510 may be identified with crosshairs or another marker, and the camera field of view adjusted to align the marker with the desired region for selection. The luminance or chromaticity of the selected image pixel or region may then be displayed as a motion plot 520 as a function of time. This luminance or chromaticity may be the luminance or chromaticity of the original image data, or of a combination of the original video data and the overlaid image data.

By comparing motion plot 520 with the known pattern or signature of tracings produced by pulsation of a jugular vein, the operator can verify that the observed motion is indeed being caused by a jugular vein. In some embodiments, the computer program itself can analyze the tracing of the object's motion to verify that it matches the motional signature of a jugular vein, thereby eliminating the need for a skilled operator to make a determination as to whether the motion is indicative of venous pulsations.

FIG. 5 also shows that interface 500 may simultaneously display an electrocardiogram 530 of the patient, or other data indicative of the cardiac activity of the patient. This simultaneous display of electrocardiogram 530 may allow the electrical activity of the heart to be compared in almost real time with the pulsations of the selected region of the neck. In some embodiments, the electrocardiogram data may be transmitted wirelessly to the computer from a wearable device worn or otherwise in contact with or adjacent to the patient. Such a wearable device may be, for example, a fitness monitor worn on the wrist of a patient, or a device held between the hands of the patient, or a device in contact with the chest of the patient, although any other suitable device may also be used to provide the cardiac data.

In some embodiments, the electrocardiogram 530 or information derived from cardiac data can also be presented audibly, so that the relative timing of the venous pulsation and the electrocardiogram can be compared by listening to them, and allowing the user to focus on the motional indicators in video display region 510. The operator may use this auditory information to verify that the observed pulsations of the selected region are due to pulsations of the jugular vein, rather than pulsations of the carotid artery. This verification can be done by a trained operator, or by using the computer program to recognize various portions of the electrocardiogram cycle, for example, the peak of the R wave, as discussed in greater detail with respect to FIG. 6.

FIG. 5 shows that the interface can include various controls 540 along with a filter control 550. Filter control 550 may allow an operator to set or modify a filter threshold so that all portions of the image whose motion exceeds this threshold can be color coded.

Figure 6:
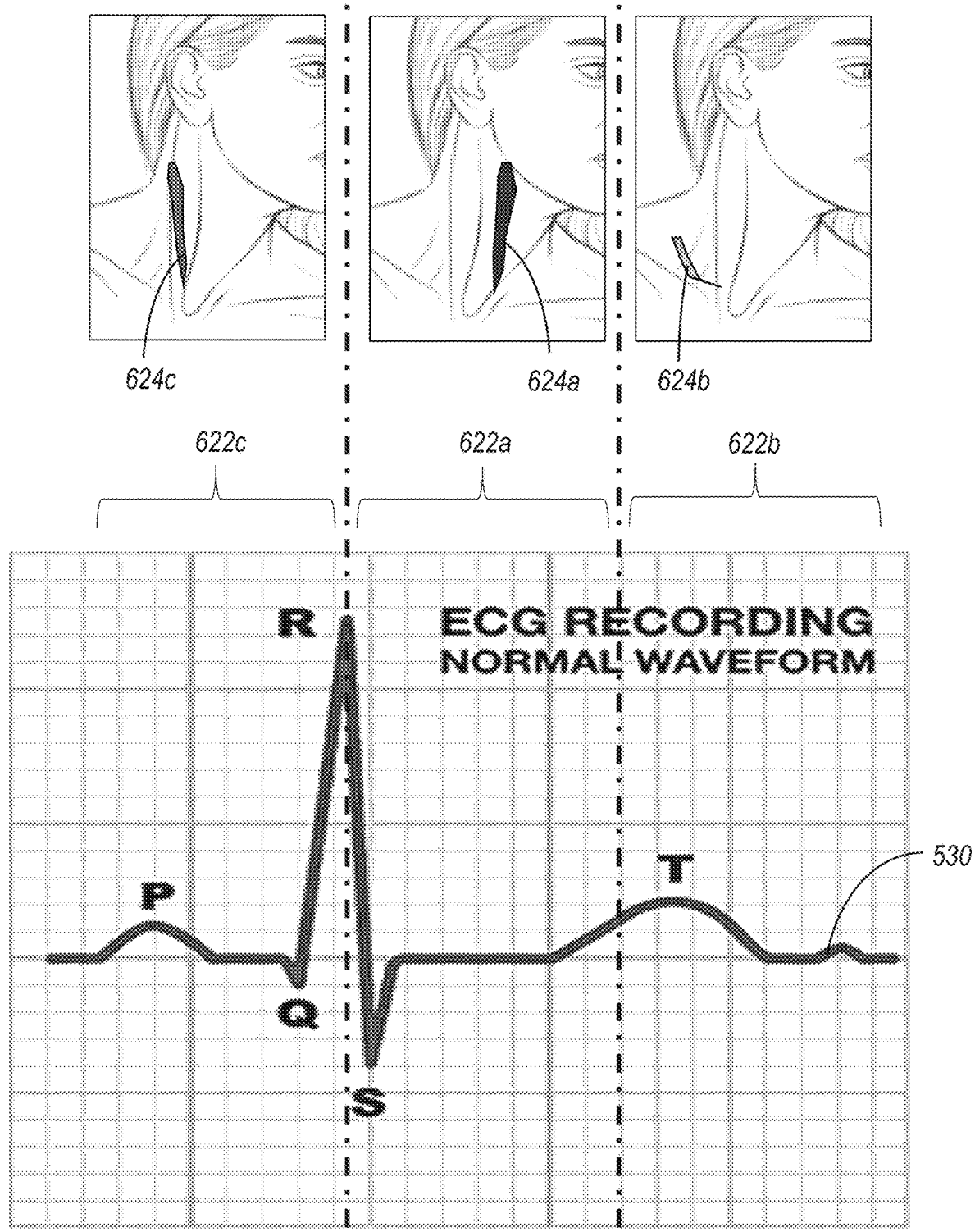
FIG. 6 illustrates color coding of overlaid image data based at least in part on cardiac data.

FIG. 6 illustrates that the color coding of the overlaid image data may be dependent at least in part on the cardiac data, such as an electrocardiogram. The color of the coding can be made to change according to the relative timing of the motion compared to the electrical activity of the heart. The patient's electrocardiogram can be made available to the program via a device such as a wireless transmitter held by the patient or strapped to the patient's wrist, as described above. The characteristic spike seen in an electrocardiogram is referred to as the R wave, and the R-wave marks early ventricular depolarisation and the beginning of ventricular contraction.

Let the average time between adjacent heartbeats, often referred to as the R-R interval, be called Δt. Pixels whose motion peaks within the first time interval Δt/3 after an R wave are colored to indicate arterial motion. This arterial window is labeled as window 622a in FIG. 6, and the arterial motion is colored in a first color 624a. In some embodiments, arterial motion may be colored as red. Pixels whose motion occurs in the subsequent time interval Δt/3, labeled as window 622b in FIG. 6, are colored a second color 624b, such as white. Pixels whose motion peaks in the final time interval Δt/3, labeled as window 622c in FIG. 6, are colored in a third color 624c, such as blue, to indicate venous motion.

The precise division of the R-R interval Δt does not necessarily have to be into equal thirds, and the temporal divisions can be tailored and shifted as needed. This use of the cardiac data in the generation of the overlay data, may allow, for example, the image of a pulsing vein to appear blue, while the image of a pulsing artery may appear red. Motion that occurs in neither the venous nor arterial portions of the cardiac cycle may be colored white. This or other suitable color coding will allow the observer to more easily differentiate a pulsing vein from a pulsing artery. In some embodiments, a software or hardware module of the computing device may use spatial image processing to alter the appearance of moving objects in the scene. In some embodiments, the spatial imaging may consist of blurring the scene by, for example, taking an average of neighboring pixels, where the size of each blurred neighborhood is adjusted to optimize a tradeoff between image resolution and processing speed. The corresponding blurred area on the surface of the neck may in some embodiments consist of between 0.01 to 1 square centimeters. In one exemplary embodiment, using each blurred region on the neck to be 0.5 cm$^2$, the resulting frame rate of the displayed image on the computer screen may be about 24 frames per second. In another exemplary embodiment, the size of each neighborhood of pixels that is averaged to produce blurring may consist of a 3-pixel-by-3-pixel square, although in other embodiments, larger groups of pixels may be used. In some embodiments, groups of pixels other than square groups of pixels may be averaged, such as rectangular groups or other shapes.

In some embodiments, the spatial image processing may be performed by implementing a Laplacian pyramid, as explained by Burt, P. and Adelson, E. "The Laplacian pyramid as a compact image code," IEEE Trans. Comm. 31, 4, 532-540 [1983], the disclosure of which is hereby incorporated by reference in its entirety. In some embodiments, the frame rate may be greater than 10 frames per second to reduce or eliminate flickering of the displayed image.

Each spatially-processed image may then be temporally processed using an algorithm that acts as a temporal bandpass filter, enhancing certain temporal frequencies and attenuating others. Such temporal bandpass filters are described in textbooks such as, *The Scientist and Engineer's Guide to Digital Signal Processing, 2$^{nd}$ Edition* by Steven W. Smith, Ph.D., California Technical Publishing [1999], and in scientific papers such as "Digital filter design for electrophysiological data—a practical approach" A. Widmann, E. Schröger, and B. Maess, J. of Neuroscience Methods, Vol. 250, pp. 34-46 [2015]. The disclosure of each of these documents is hereby incorporated by reference in its entirety.

In one exemplary embodiment, for an Nth-order temporal filter, a possible recursive algorithm is:

$$Y(n) = \sum_{i=0}^{N} b_i X(n-i) - \sum_{i=1}^{N} a_i Y(n-i)$$

where Y(n) is the nth filtered video frame, and X(n) is the nth unfiltered video frame.

The coefficients $a_i$ and $b_i$ above will set the upper and lower frequencies of the temporal filter. If the temporal filter is a frequency bandpass filter, the optimum frequency passband is affected by the pulse rate of the patient. For example, if the patient's pulse rate is 60 beats per minute (=1 Hz), and if the effective frame rate of the video camera is 24 frames per second, then a desired frequency passband may lie between approximately 0.8 Hz and 4 Hz. This frequency passband can be achieved by using a second-order filter (N=2) in the equation above and setting $b_0$=0.4667, $b_1$=0.0000, $b_2$=−0.4667, $a_1$=−0.9446, and $a_2$=0.0667. A wide variety of other suitable filters and filter parameters may also be used in other embodiments, however.

The temporal frequency-filtered image enhances moving regions of the video, which may in some embodiments be a video to which a spatial filter was previously applied, and in some embodiments may be a video which has not had a spatial filter applied. In some embodiments, the computing device can be configured to preferentially highlight those pixels whose motion exceeds set thresholds. These thresholds can be set by the operator. For example, if the video pixels use a RGBA color space, then any filtered pixels whose red or green or blue or alpha values exceed set thresholds may be selected and highlighted. The program may overlay these highlighted pixels superimposed on the original image so that the location of the pulsing objects can be seen in relation to the rest of the patient, especially the patient's neck.

In some embodiments, using a touch-screen or a cursor, the observer can select a small area of pixels in the image and study the motion of that selected region in more detail. The program may compute and store the magnitude of the motion of the selected pixel region continuously and display it in motion plot 520 as a function of time. For example, in one embodiment, selecting the "Review" button from controls 540 of interface 500 illustrated in FIG. 5 may bring up a review interface such as the review interface shown in FIG. 7. This review interface 700 may allow the user to select and review motion plot 520.

Figure 7:
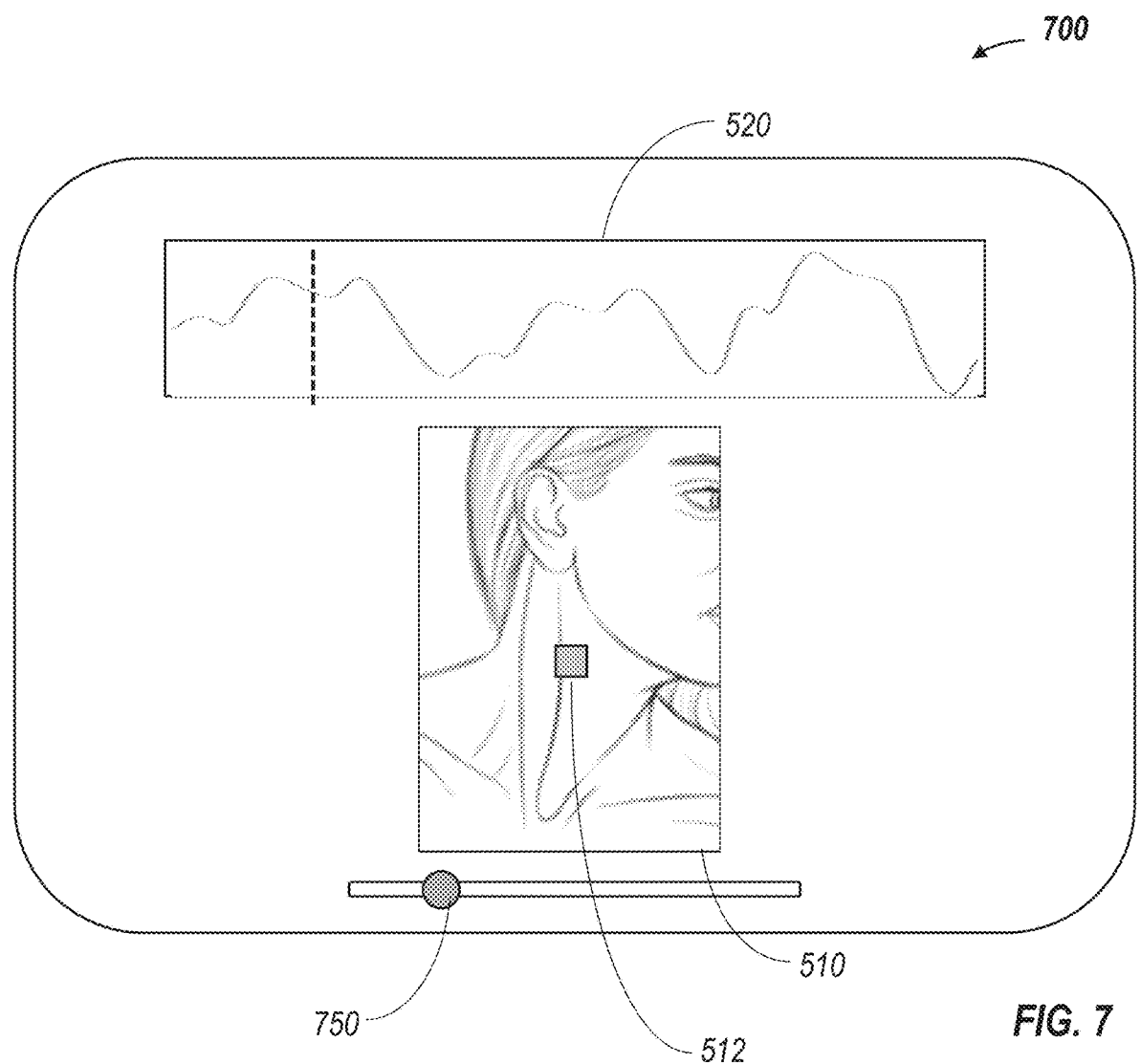
FIG. 7 illustrates another exemplary interface format for a system for determining the CVP of a patient.

The window in FIG. 7 may include video display region 510 which may display motion-adjusted video, such as the colored overlay data shown in FIG. 6. Review interface 700 may also display motion plot 520 of the selected pixel on the patient's neck. Motion plots due to venous pulsation may have a characteristic double peak, while motion plots due to arterial pulsation usually has a single peak. This additional information can help the observer decide whether the motion of the selected neighborhood is indicative of venous or arterial pulsations. By scrolling through motion plot 520 in conjunction with the image data in the video display region, the observer can also observe the measured pulsations in slow motion, allowing the precise location of the pulsations on the neck to be determined. Controls 750 may be used to control this scrolling process. In other embodiments, a review interface may include an electrocardiogram or information derived from cardiac data, in addition to or in place of motion plot 520.

As the central venous pressure changes over time, the distalmost location of the pulsation on the neck changes. A useful diagnostic data point is the location of the top of the venous pulse at the instant when the central venous pressure is in its local pressure trough between its a-wave and c-wave pressure peaks. Using the display screen pictured in FIG. 7, the observer can scroll through motion plot 520 in slow motion to determine a precise location of the top of the pressure pulsations in video display region 510 when the central venous pressure is at various pressure values between its a-wave and c-wave pressure peaks.

Once the pulsations of the jugular vein have been identified, the angle θ of the tilt table may be adjusted until, when the venous pulsation is between its a-wave and c-wave pressure peaks, the top of the venous pulsations appear at the midpoint of the patient's neck, that is, midway between the mandible and the clavicle. The central venous pressure in units of cm of water may then be computed, such as by using the following formula:

$$\text{Pressure} = L \sin \theta + D \cos \theta$$

where L is the distance in cm from the angle of Louis (manubrium-sternal junction) to the midpoint of the patient's neck, and the distance D is from the angle of Louis to the right atrium. For an average size person L≈15 cm. However, this distance L may also be measured, particularly if the patient is significantly smaller, such as a child, or larger, such as a tall basketball player. The distance D can be approximated as D=5 cm for everyone. Setting L≈15 cm, Table 1 shows the computed central venous pressure as a function of the angle of the tilt table.

TABLE 1

| tilt angle (degrees) | Central venous pressure (cm of water) |
| --- | --- |
| 0 | 5.0 |
| 5 | 6.3 |
| 10 | 7.5 |
| 15 | 8.7 |
| 20 | 9.8 |
| 25 | 10.9 |
| 30 | 11.8 |
| 35 | 12.7 |
| 40 | 13.5 |
| 45 | 14.1 |
| 50 | 14.7 |
| 55 | 15.2 |
| 60 | 15.5 |
| 65 | 15.7 |
| 70 | 15.8 |
| 75 | 15.8 |
| 80 | 15.6 |
| 85 | 15.4 |
| 90 | 15.0 |

Figure 8:
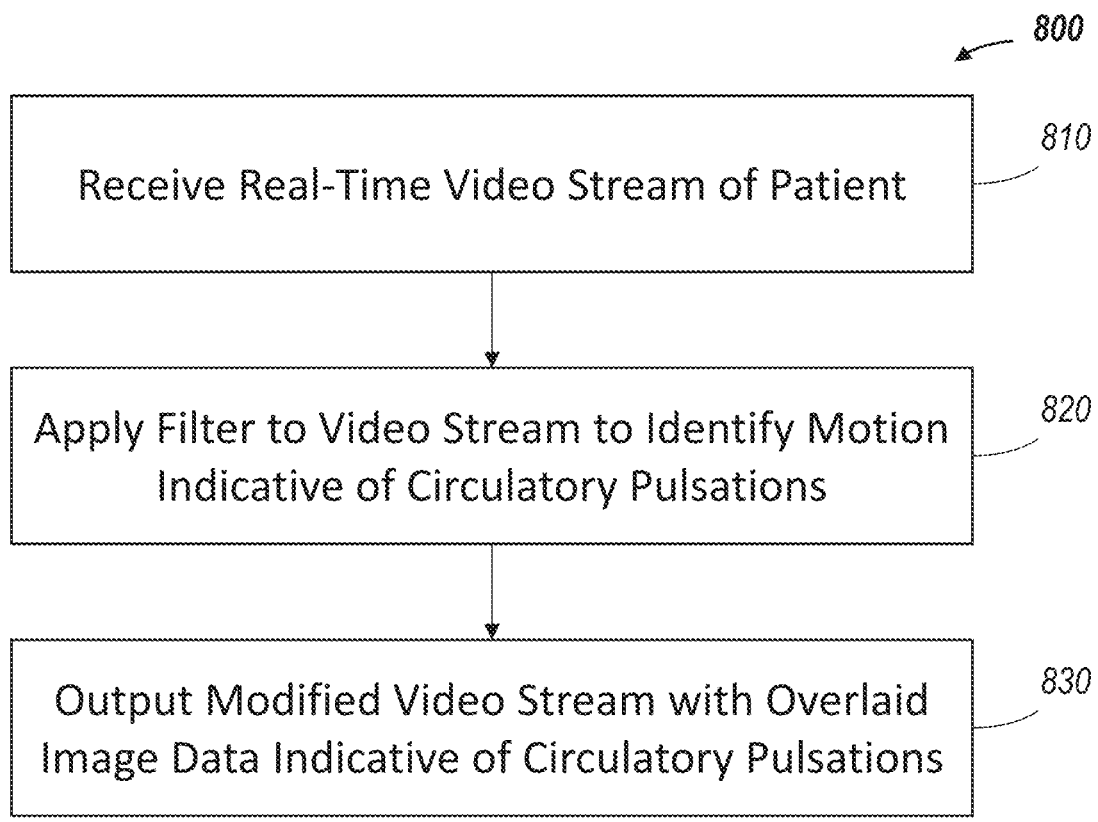
FIG. 8 is a flow diagram schematically illustrating certain steps in a process for modifying a video stream to highlight circulatory pulsations of a patient.

FIG. 8 is a flow diagram schematically illustrating certain steps in a process for modifying a video stream to highlight circulatory pulsations of a patient. The process 800 begins at a stage 810 where a real-time video stream of a patient is received by a computing device. The real-time video stream may be received from an integrated camera within a computing device, or from an external camera or other device. As discussed above, at least the neck region of a patient may be visible in the real-time video stream.

The process 800 moves to a stage 820 where a filter is applied to the real-time video stream by the computing device. The parameters of the filter may be configured to identify motion indicative of circulatory pulsations. In some embodiments, at least some of the parameters may be preconfigured. In some embodiments, at least some of the parameters may be adjusted from preconfigured parameters in response to user input. In some embodiments, applying a filter to the real-time video stream may include applying a spatial filter to the video stream prior to applying a temporal filter to the video stream.

It will be understood that in some embodiments, the motion need not necessarily be characterized by the processor as indicative of circulatory pulsations. However, applying the filter may allow a user to identify such motion. Additional context, such as the location relative to the neck of such motion, or the simultaneous display of images or audio relating to the cardiac activity of the patient, may aid the user in making such a determination.

The process 800 moves to a stage 830 where the computing device outputs a modified video stream. Because the process may include the use of a computationally efficient filter, the computing device may keep up with the video stream, allowing the filter or filters to be applied substantially in real-time. Thus, the modified video stream may be outputted substantially in real-time. The modified video stream may be displayed on an integrated display, or may be communicated to an external display for substantially real-time display.

Figure 9:
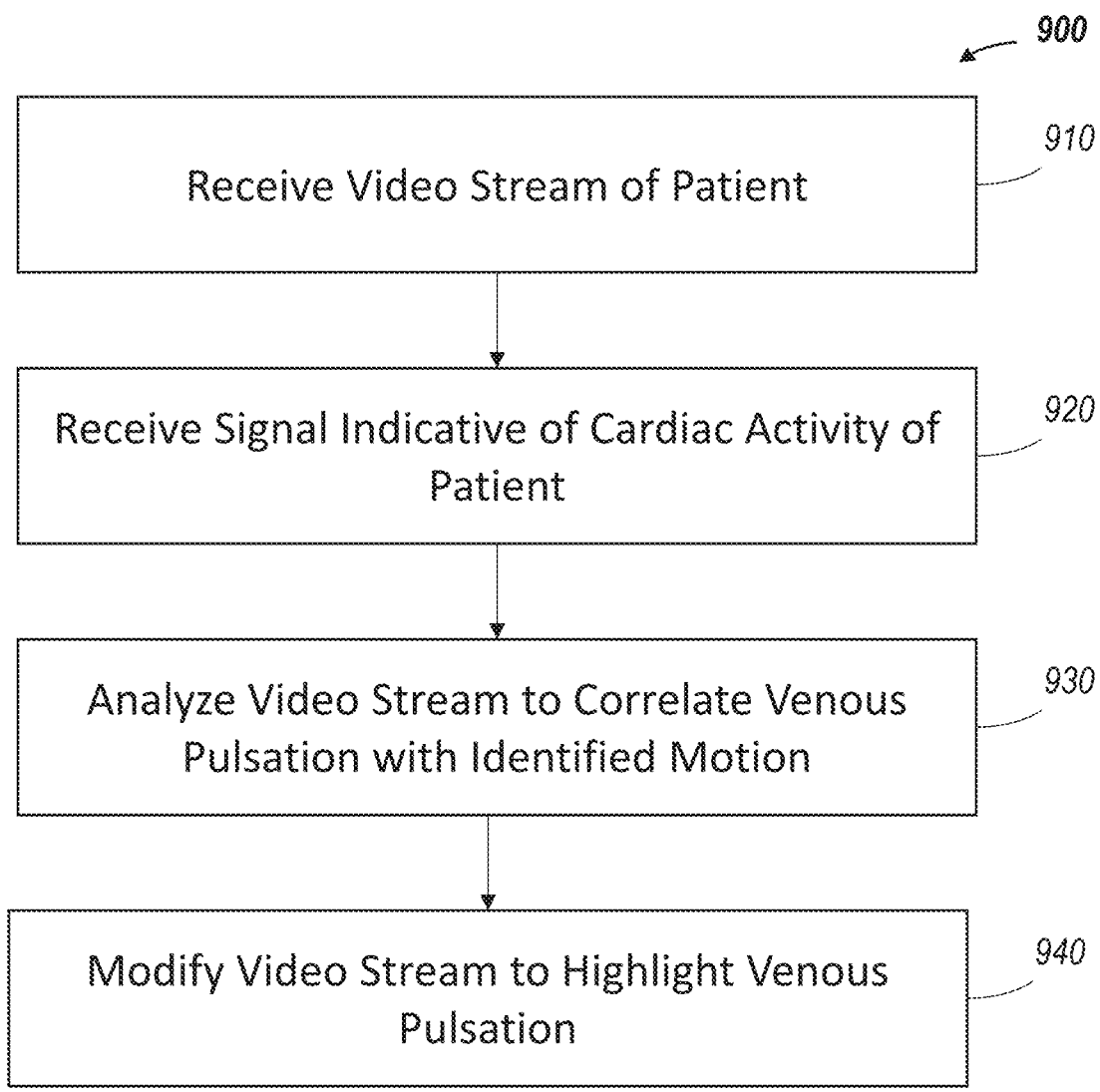
FIG. 9 is a flow diagram schematically illustrating certain steps in a process for processing video data by a processing device to provide overlaid image data enhancing the display of venous pulsations of a patient.

FIG. 9 is a flow diagram schematically illustrating certain steps in a process for processing video data by a processing device to provide overlaid image data enhancing the display of venous pulsations of a patient. The process 900 begins at a stage 910 where a video stream of a patient is received by a computing device. The video stream may be a real-time video stream received from an integrated camera within a computing device, or from an external camera or other device. The process 900 moves to a stage 920 where a cardiac signal indicative of the cardiac activity of the patient is received. The cardiac signal may in some embodiments be electrocardiogram data. The cardiac signal may be received from a dedicated monitoring device.

The process 900 moves to a stage 930 where the video stream is analyzed to detect motion indicative of venous pulsations of the patient. This may include the application of a filter to the video stream to identify motion indicative of circulatory pulsation of the patient. This may also include analysis of the cardiac data to determine whether or not motion is indicative of venous pulsation, rather than arterial pulsation or other movement. For example, the cardiac data may be analyzed to identify windows of time within which motion is likely to correspond to venous pulsations, and windows of time within which venous pulsation is not likely to occur. The process can also include analysis of the spatial extent of the pulsation.

The process 900 moves to a stage 940 where the computing device outputs a modified video stream highlighting motion indicative of venous pulsations of the patient. In some embodiments, venous pulsations may be highlighted in a different color, or in another fashion visually distinguishable from other highlighted motion. In some embodiments, only motion likely to be indicative of venous pulsation may be highlighted, and other motion may be not highlighted. The modified video stream may be outputted substantially in real-time and may be displayed on an integrated display, or may be communicated to an external display for substantially real-time display.

Figure 10:
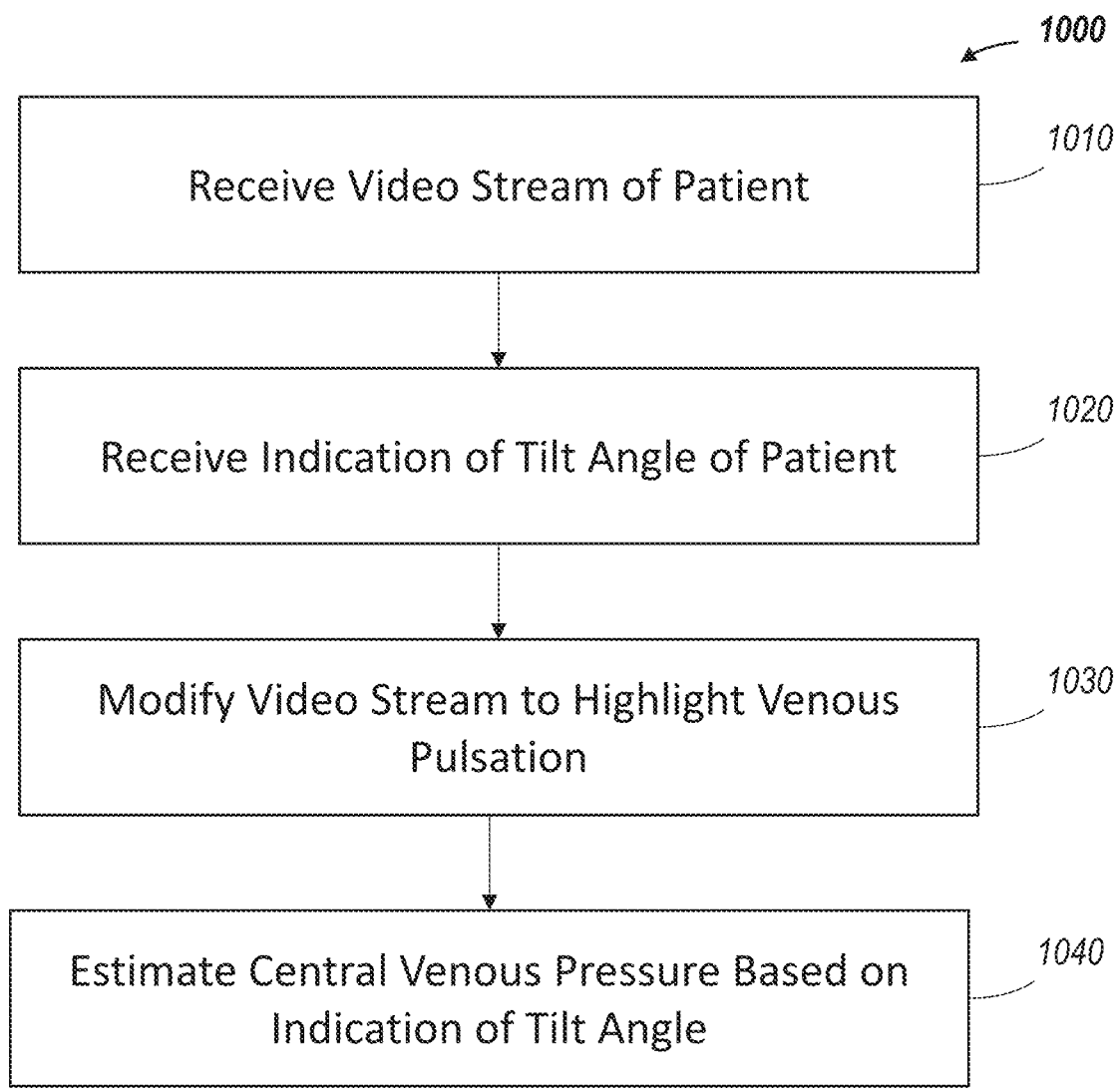
FIG. 10 is a flow diagram schematically illustrating certain steps in a process for estimating a central venous pressure of a patient.

FIG. 10 is a flow diagram schematically illustrating certain steps in a process for estimating a central venous pressure of a patient. The process 1000 begins at a stage 1010 where a video stream of a patient is received by a computing device. The video stream may be a real-time video stream as discussed above. Process 1000 moves to a stage 1020 where an indication of the tilt angle of the patient at a corresponding point in the video stream is received. In some embodiments, the indication of the tilt angle may be provided via user input. In some embodiments, the computing device may measure the tilt angle of the patient, such as through the use of internal sensors of the computing device. In some embodiments, the computing device may measure the tilt angle of the patient based at least in part on the received video stream.

At a stage 1030, the video stream is modified to highlight motion including motion indicative of venous pulsation. In some embodiments, motion indicative of venous pulsation is identified separately from other motion, including arterial pulsations. In such embodiments, the detection of such motion can involve the use of additional information indicative of the cardiac activity of the patient.

The identification of motion indicative of venous pulsation can be used, either by the computing device or by a user, to determine whether the patient is in a representative position from which the central venous pressure can be estimated. The representative position may be, for example, a position in which the venous pulsations extend to the midpoint of the neck of the patient.

In some embodiments, the computing system may make a determination as to whether the patient is in a representative position. This determination may be facilitated by a previous identification of a specific location on the neck of the patient corresponding to the representative position of the patient. For example, if the computing device is configured to estimate central venous pressure when the patient is in a position where the venous pulsation extends to the midpoint of the neck, a user may mark the midpoint of the neck to facilitate this determination by the computing device. In other embodiments, the computing device may process the video stream to identify the midpoint or another representative location of the patient.

Upon a determination that the patient is in a representative position, process 1000 moves to a stage 1040 where the central venous pressure of the patient is estimated. This estimation may be based on the previously received indication of the tilt angle of the patient. If a determination is made that the patient is not in a representative position, the tilt angle of the patient may be adjusted, and the process repeated until the patient is determined to be in a representative position. The central venous pressure of the patient may then be estimated.

In the foregoing description, specific details are given to provide a thorough understanding of the examples. However, it will be understood by one of ordinary skill in the art that the examples may be practiced without these specific details. Certain embodiments that are described separately herein can be combined in a single embodiment, and the features described with reference to a given embodiment also can be implemented in multiple embodiments separately or in any suitable subcombination. In some examples, certain structures and techniques may be shown in greater detail than other structures or techniques to further explain the examples.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for processing video data by a processing device to provide overlay image data enhancing the display of venous pulsations of a patient, the system comprising a processor and a memory, the system configured to:
   receive a real-time video stream comprising image data of a patient;
   apply a filter to the video stream to facilitate detection of changes between frames of the image data indicative of circulatory pulsations of the patient; and
   outputting a modified video stream substantially contemporaneously with the reception of the video stream, the modified video stream comprising overlay image data indicative of circulatory pulsations of the patient and enhancing the display of venous pulsations of the patient relative to other movement in the video stream.

2. The system of claim 1, wherein applying a filter to the video stream comprises applying a temporal bandpass filter to the video stream.

3. The system of claim 1, wherein applying a filter to the video stream comprises applying a spatial filter to the video stream prior to applying a temporal filter.

4. The system of claim 1, wherein the system is further configured to receive a cardiac signal, the cardiac signal indicative of cardiac activity of the patient as a function of time during capture of the video stream, wherein the overlay image data is generated at least in part on the received cardiac signal.

5. The system of claim 4, wherein the system is further configured to identify at least one venous-pulsation time window and at least one arterial-pulsation time window based on the cardiac signal, wherein the overlay image data is generated based at least in part on the identified venous-pulsation time window and the identified arterial-pulsation time window.

6. The system of claim 4, wherein the cardiac signal comprises electrocardiogram data.

7. The system of claim 1, wherein the overlay image data highlights motion indicative of venous pulsations of the patient in a first color and other motion in at least one other color distinct from the first color.

8. The system of claim 1, wherein the system is configured to record an indication of movement within a subregion of the video stream and display a plot of the movement within the subregion of the video stream over time, and wherein the subregion of the video stream is identified based at least in part on user input.

9. The system of claim 1, wherein the system is further configured to:
 receive an indication of the tilt angle of a neck region of the patient;
 analyze the video stream to identify motion indicative of venous pulsation of the patient; and
 in response to an indication that the patient is at a representative tilt angle at which a central venous pressure of the patient can be estimated by analyzing the video stream, estimating the central venous pressure of the patient based at least in part on the indication that the patient is at a representative tilt angle.

10. The system of claim 9, wherein the system is configured to receive the indication that the patient is at a representative tilt angle from user input.

11. The system of claim 9, wherein the system is further configured to generate overlay data distinguishing the identified motion indicative of venous pulsation from other identified motion in the video stream.

12. The system of claim 9, wherein the system is configured to determine that the patient is at a representative tilt angle without user input subsequent to reception of the video stream.

13. The system of claim 9, wherein the representative tilt angle corresponds to a position in which the venous pulsations extend to roughly the midpoint of the neck of the patient.

14. A method of processing video data by a processing device to provide overlaid image data enhancing the display of venous pulsations of a patient, the method comprising:
 receiving a video stream comprising image data of a patient;
 receiving a cardiac signal indicative of the cardiac activity of the patient as a function of time;
 analyzing the video stream to detect motion indicative of circulatory pulsations of the patient;
 modifying the video stream to highlight motion indicative of venous pulsations of the patient relative to other movement in the video stream.

15. The method of claim 14, wherein analyzing the video stream comprises analyzing the video stream based at least in part on the cardiac signal.

16. The method of claim 14, wherein the cardiac signal comprises an electrocardiogram signal.

17. The method of claim 14, wherein receiving the cardiac signal comprises wirelessly receiving the cardiac signal.

18. The method of claim 14, wherein analyzing the video stream comprises:
 applying a temporal filter to the video stream to identify motion indicative of circulatory pulsations; and
 analyzing the cardiac signal to characterize the detected motion as indicative of arterial or venous pulsations.

19. The method of claim 18, wherein analyzing the video stream comprises applying a spatial filter to the video stream prior to application of the temporal filter to the video stream.

20. The method of claim 18, wherein modifying the video stream to highlight the motion indicative of venous pulsations of the patient comprises highlighting the motion indicative of venous pulsations of the patient in a first color and highlighting motion indicative of arterial pulsations in a second color distinct from the first color.

* * * * *